US00PP10537P

United States Patent [19]

Danziger

[11] Patent Number: Plant 10,537

[45] Date of Patent: Aug. 4, 1998

[54] NEW GUINEA IMPATIENS PLANT NAMED 'DANIBOSS'

[75] Inventor: Gaby Danziger, Nir Zvi, Israel

[73] Assignee: Danziger - "Dan" Flower Farm, Post Beit Dagan, Israel

[21] Appl. No.: 677,852

[22] Filed: Jul. 10, 1996

[51] Int. Cl.[6] ..... A01H 5/00

[52] U.S. Cl. ..... Plt./87.6

[58] Field of Search ..... Plt./87.6

[56] References Cited

U.S. PATENT DOCUMENTS

P.P. 8,262 6/1993 Dehan ..... Plt./87.6

*Primary Examiner*—Howard J. Locker
*Assistant Examiner*—Kent L. Bell
*Attorney, Agent, or Firm*—Foley & Lardner

[57] ABSTRACT

A new and distinct cultivar of impatiens plant named 'Daniboss', characterized by the combined features of bright red-purple flower color, very large flowers, solid dark red-green leaves, round, very compact growth habit with excellent self branching, and by its unique leaves, which are more round and thicker than other known cultivars of the species.

1 Drawing Sheet

The present invention relates to a new and distinctive cultivar of Impatiens plant, botanically known as Impatiens, commercially known as New Guinea Impatiens and known by the cultivar name 'Daniboss'.

Daniboss was developed by the inventor Gaby Danziger in a controlled breeding program in Mishmar Hashiva, Israel by crossing the cultivar identified as '6-73' (seed parent), with the cultivar identified as '5-52' (pollen parent). Both cultivars are proprietary.

Asexual reproduction of the new cultivar by leaf cuttings taken by the inventor at Mishmar Hashiva, Israel has shown that the unique features of this new Impatiens plant are stabilized and are reproduced true to type in successive propagations.

The following characteristics in combination distinguish the new impatients plant from both its parent varieties and other cultivated impatients of this type known and used in the floriculture industry:

1. Red-purple flower color, with a lighter center.
2. Large, round flowers.
3. Solid dark red-green leaves, significantly rounder than most New Guinea cultivars.
4. Very compact and round growth habit, with very good self branching.
5. The leaves are thicker compared to the leaves of other New Guinea cultivars.

In the accompanying colored photographic drawings, the photograph at the top of the sheet comprises a top view showing the overall appearance of the new cultivar, with the photograph at the bottom of the page showing flowers and foliage in much greater detail. Neither photograph shows consistently the true flower color, which as noted below is closest to bright red-purple 66A. That color appears in the close-up photo but not consistently due to unavoidable photographic error. It is anticipated that this plant will be marketed under the trademark "Bossa Nova".

When compared to the cultivar Dandin, disclosed in U.S. Plant Pat. No. 8,262, Daniboss is more compact, it has a significantly darker flower color, and it flowers later than Dandin when the cultivars are grown under similar conditions.

The following is a detailed description of my new impatiens cultivar based on plants produced under commercial practice in Mishmar Hashiva, Israel. The plants were grown in a net covered greenhouse during spring time, with a maximum temperature of 30° C. and a minimum temperature of 18° C.

Color references are made to The Royal Horticultural Society colour chart except where general terms of ordinary dictionary significance are used.

Parentage: Seedling from '6-73'×'6-52'.

Propagation:

*Type cutting.*—Leaf cuttings.

*Time to initiate roots.*—7–8 days at 25° C. in summer and 8–9 days at 20° C. in winter.

*Rooting habit.*—Roots well, about 20–25 roots per plant, each approximately 2–4 in length and 0.5–1.0 mm thick.

Plant description:

*Form.*—Plant is relatively large in diameter, with good self branching. As measured 4 months after planting a single young plant in a 16 cm pot, the plant was approximately 15–20 cm in height and 20–50 cm in width.

*Habit.*—Compact and round.

*Foliage (mature).*—Size: Approximately 85 mm long and 48 mm wide: leaves are wider and rounder than leaves of most New Guinea cultivars, leaf apex is acuminate and base is acuminate; texture is typical for the species. Shape: Ovate. Margin: Serrated. Color: Young foliage: Topside 139A but heavily infused with red to give a red-green color not shown in R.H.S.; underside 185A. Mature foliage: Topside is generally the same color as for young foliage; underside 185A at the margin, greener at the center. Venation: The main vein is red. The main vein is approximately 1.0 mm thick at base and becomes narrower toward top of leaf; secondary veins are pinnate and very thin on upper surface and thicker on under surface; under surface color is red.

Flowering description:

*Flowering habits.*—Flowers develop above the foliage, and cover the entire plant.

*Natural flowering season.*—Flowering is year round in temperatures between 5C and 25C; not tolerant to frost.

*Flower buds.*—Buds carried on long green (R.H.S. 143C) pedicels 45 mm in length, with red spurs (R.H.S. 47B). There are 3–5 bus on each axil, with the buds being oval and 1.5 cm in major direction; spur is half-rounded and 3.0–3.5 cm in length.

*Flower borne.*—The flowers are carried on strong stems that terminate well above the foliage. Flowering commences about 50–51 days days after planting under normal growing conditions.

*Quantity of flowers.*—Medium.

*Petals.*—Shape: Typical, with two heart-shaped pairs of petals, with each petal being approximately 2.5–3.0 cm in width and 2.5–2.7 cm in length; the remaining petal is relatively larger at 4.0 cm in width and 2.0 cm in length. Color: Top side when opening is closest to 66A but not precisely shown in the color chart; there is no fading; under side 52A; claw color is pink. Number of petals: 5. Size of flowers: Very large, approximately 6.0 cm in diameter.

*Reproductive organs.*—Stamens: One (1) in number. Another shape: Round, color 52A Pollen color: White. Pistils: Stigma shape: Round, color red. Style color: Green. Ovaries: Four, 1 mm in size, green in color.

*Disease resistance.*—No abnormal disease problems have been noticed to date.

I claim:

1. A new and distinct cultivar of Impatiens plant named 'Daniboss', as illustrated and described.

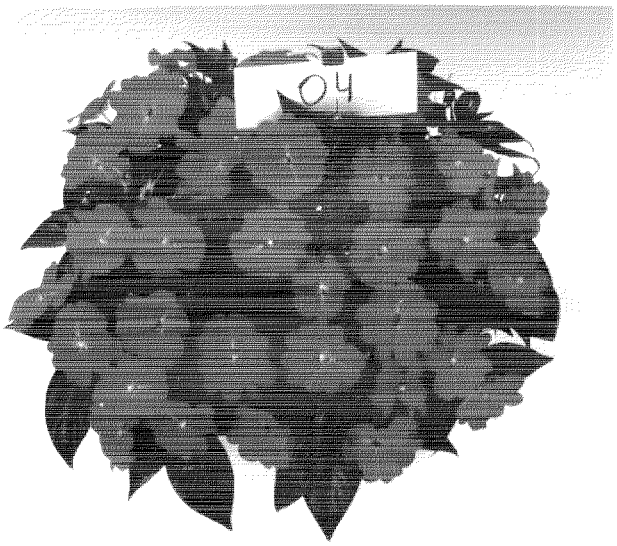
04
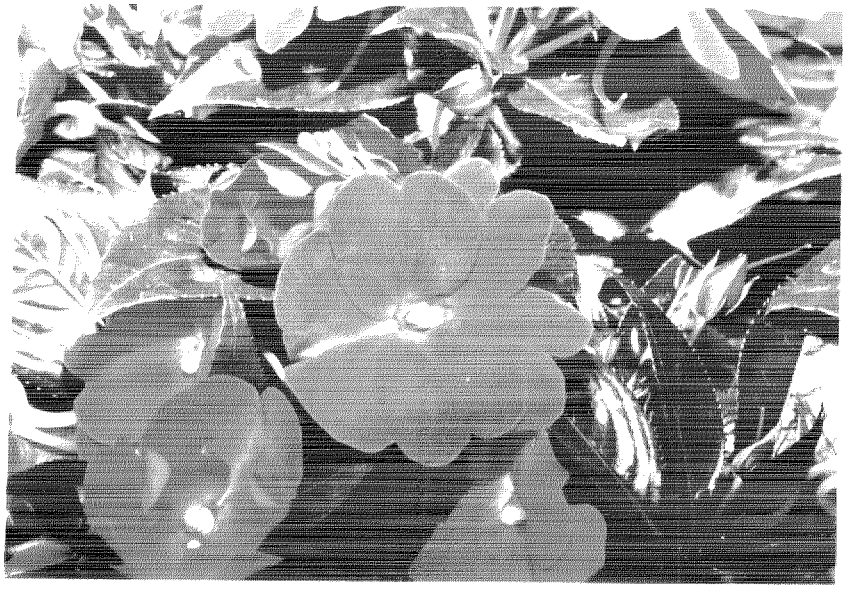

* * * * *